(12) United States Patent
Arcos et al.

(10) Patent No.: US 12,127,952 B2
(45) Date of Patent: Oct. 29, 2024

(54) INTERVERTEBRAL DEVICES

(71) Applicant: AXIS SPINE TECHNOLOGIES LTD, St. Albans (GB)

(72) Inventors: Jonathan Arcos, St. Albans (GB); Christopher Reah, St. Albans (GB)

(73) Assignee: AXIS SPINE TECHNOLOGIES LTD, St. Albans (GB)

( * ) Notice: Subject to any disclaimer, the term of this patent is extended or adjusted under 35 U.S.C. 154(b) by 683 days.

(21) Appl. No.: 17/430,711

(22) PCT Filed: Feb. 12, 2020

(86) PCT No.: PCT/GB2020/050328
§ 371 (c)(1),
(2) Date: Aug. 12, 2021

(87) PCT Pub. No.: WO2020/165586
PCT Pub. Date: Aug. 20, 2020

(65) Prior Publication Data
US 2022/0142791 A1    May 12, 2022

(30) Foreign Application Priority Data

Feb. 13, 2019  (GB) ..................................... 1902002

(51) Int. Cl.
*A61F 2/44*    (2006.01)
*A61F 2/30*    (2006.01)
(52) U.S. Cl.
CPC ..... *A61F 2/447* (2013.01); *A61F 2002/30112* (2013.01); *A61F 2002/30148* (2013.01);
(Continued)
(58) Field of Classification Search
None
See application file for complete search history.

(56) References Cited

U.S. PATENT DOCUMENTS 6,045,579 A    4/2000  Hochshuler et al.
6,102,950 A    8/2000  Vaccaro
(Continued)

FOREIGN PATENT DOCUMENTS

DE    102012023042 X    11/2013
EP         2719360        4/2014
(Continued)

OTHER PUBLICATIONS

Product Brochure "Aero-LL Lateral Lumbar Interbody and Fixation System", Stryker Spine, 2016, pp. 1-52.
(Continued)

*Primary Examiner* — Tessa M Matthews
(74) *Attorney, Agent, or Firm* — LIU & LIU

(57) ABSTRACT

The intervertebral fusion device (200) comprises a superior component (220), an inferior component (240) and a core component (260). The superior and inferior components (220, 240) are received in an intervertebral space between first and second vertebrae whereby the superior component top side abuts against the first vertebra, the inferior component bottom side abuts against the second vertebra, and the superior component bottom side and the inferior component top side oppose each other. A height of the intervertebral fusion device is determined upon insertion of the core component (260) between the superior and inferior components (220, 240). Each of the superior component top side and the inferior component bottom side is one of: oblong having a major axis; and square, being bounded by four edges. During insertion of the core component (260) a first core profile of the core component cooperates with a superior component profile at the superior component bottom side and a second core profile of the core component cooperates with an inferior component profile at the inferior component top side whereby the core component moves in (Continued)

a direction oblique to the major axis where the superior component top side or the inferior component bottom side is oblong or to an edge of the superior component top side or the inferior component bottom side where the superior component top side or the inferior component bottom side is square.

20 Claims, 6 Drawing Sheets

(52) U.S. Cl.
CPC ............... *A61F 2002/30153* (2013.01); *A61F 2002/30154* (2013.01); *A61F 2002/30158* (2013.01); *A61F 2002/30266* (2013.01); *A61F 2002/30398* (2013.01)

(56) References Cited

U.S. PATENT DOCUMENTS

| | | | |
|---|---|---|---|
| 6,113,637 | A | 9/2000 | Gill et al. |
| 8,308,804 | B2 | 11/2012 | Krueger |
| 8,388,686 | B2 | 3/2013 | Aebi et al. |
| 9,402,739 | B2 | 8/2016 | Weiman et al. |
| 9,526,628 | B2 | 12/2016 | Krueger |
| 9,585,765 | B2 | 3/2017 | Niemiec et al. |
| 9,801,734 | B1 | 10/2017 | Stein et al. |
| 2002/0143399 | A1 | 10/2002 | Sutcliffe |
| 2003/0187506 | A1* | 10/2003 | Ross .................... A61F 2/4465 623/17.13 |
| 2004/0254644 | A1 | 12/2004 | Taylor |
| 2005/0165485 | A1* | 7/2005 | Trieu ...................... A61F 2/442 623/17.13 |
| 2006/0015183 | A1* | 1/2006 | Gilbert ................. A61F 2/4425 623/17.11 |
| 2007/0270957 | A1 | 11/2007 | Heinz |
| 2007/0276498 | A1 | 11/2007 | Aebi et al. |
| 2008/0046083 | A1* | 2/2008 | Hewko ................. A61F 2/4425 623/17.16 |
| 2008/0082173 | A1 | 4/2008 | Delurio et al. |
| 2008/0294260 | A1 | 11/2008 | Gray |
| 2011/0153020 | A1 | 6/2011 | Abdelgany et al. |
| 2011/0184522 | A1 | 7/2011 | Melkent et al. |
| 2013/0006357 | A1 | 1/2013 | Krueger |
| 2013/0035763 | A1* | 2/2013 | Krueger ................ A61F 2/4684 623/17.16 |
| 2013/0085573 | A1 | 4/2013 | Lemoine et al. |
| 2013/0103153 | A1 | 4/2013 | Blackwell et al. |
| 2013/0158667 | A1 | 6/2013 | Tabor et al. |
| 2015/0164494 | A1 | 6/2015 | Glazer |
| 2015/0320568 | A1 | 11/2015 | Ameil et al. |
| 2016/0116396 | A1 | 4/2016 | Hunt et al. |
| 2016/0166396 | A1 | 6/2016 | McClintock |
| 2016/0213483 | A1 | 7/2016 | To et al. |
| 2017/0196698 | A1 | 7/2017 | Kim |
| 2017/0239063 | A1 | 8/2017 | Predick |
| 2018/0000606 | A1 | 1/2018 | Hessler et al. |
| 2018/0036141 | A1 | 2/2018 | O'Neil et al. |
| 2018/0098860 | A1 | 4/2018 | To et al. |
| 2018/0256357 | A1 | 9/2018 | To et al. |

FOREIGN PATENT DOCUMENTS

| | | |
|---|---|---|
| WO | 2013184946 | 12/2013 |
| WO | 2014093136 | 6/2014 |

OTHER PUBLICATIONS

International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.
International Search Report of Counterpart PCT International Application No. PCT/GB2020/050328.

* cited by examiner

INTERVERTEBRAL DEVICES

FIELD OF THE INVENTION

The present invention relates to intervertebral devices and more specifically to intervertebral fusion devices.

BACKGROUND ART

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure, such as spinal fusion, may be used to address such problems. A typical spinal fusion procedure involves partial or full removal of a problematic intervertebral disc and installation of an intervertebral device in the place of the partially or fully removed intervertebral disc.

Known intervertebral devices are of varied form and function. Many known intervertebral devices are configured to provide for adjustment of height and functional spine unit angle to address differing extents of removal of an intervertebral disc, differing anatomy and spinal deformity. Known intervertebral devices for anterior lumbar interbody fusion are comparatively easy to deploy in the lumbosacral joint, i.e. L5/S1, because blood vessels adjacent the lumbosacral joint separate readily to allow wide access to the intervertebral space. Deploying an anterior lumbar interbody fusion device in the next two joints in the spine, i.e. L4/5 and L3/4, is less easy because blood vessels adjacent these joints require more retraction. Furthermore, retraction of blood vessels to allow access to the intervertebral space risks damage to the blood vessels.

Oblique lateral interbody fusion devices are often preferred to anterior lumbar interbody fusion devices because less blood vessel retraction is normally required. There are two options for deploying an oblique lateral interbody fusion device. The first option involves rotation of the oblique lateral interbody fusion device after its insertion into the intervertebral space. The second option involves insertion of the oblique lateral interbody fusion device without subsequent rotation. Irrespective of whether the first option or the second option is used, an upper limit is imposed on the size of the oblique lateral interbody fusion device when it is to be inserted where there is limited room, such as in L4/5 or L3/4. An interbody fusion device of larger footprint is normally desired because a larger footprint enables the interbody fusion device to be situated over a greater extent of strong bone and, in particular, over strong bone towards the periphery of the vertebrae. Situating the interbody fusion device over strong bone reduces risk of the interbody fusion device subsequently subsiding into the adjacent vertebrae. Furthermore, the imposition of an upper limit on the size of the oblique lateral interbody fusion device limits scope for deformity correction because there may be insufficient room for insertion of a higher interbody fusion device needed for a greater correction angle.

The present invention has been devised in light of the inventors' appreciation of shortcomings of known interbody fusion devices, such as the shortcomings described above. It is therefore an object for the present invention to provide an improved intervertebral device and more specifically an improved intervertebral fusion device. It is a further object for the present invention to provide an improved method of installing an intervertebral device in an intervertebral space between first and second adjacent vertebrae and more specifically an improved method of installing an intervertebral fusion device.

STATEMENT OF INVENTION

According to a first aspect of the present invention there is provided an intervertebral fusion device comprising:
a superior component having a superior component top side and a superior component bottom side, the superior component being configured to be received in an intervertebral space between first and second vertebrae whereby the superior component top side abuts against the first vertebra;
an inferior component having an inferior component top side and an inferior component bottom side, the inferior component being configured to be received in the intervertebral space between the first and second vertebrae whereby the inferior component bottom side abuts against the second vertebra, the superior component bottom side and the inferior component top side opposing each other when the superior and inferior components are received in the intervertebral space;
a core component configured for insertion between the superior and inferior components whereby a separation between the superior and inferior components and hence height of the intervertebral fusion device are determined when the intervertebral fusion device is in the intervertebral space,
wherein each of the superior component top side and the inferior component bottom side is one of: oblong having a major axis; and square, being bounded by four edges, and
wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component being placed in the intervertebral space such that the superior component top side faces the first vertebra or what might remain of a partially removed intervertebral disc. The inferior component has an inferior component top side and an inferior component bottom side with the inferior component being placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components, as described below.

The core component is configured for insertion between the superior and inferior components. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height.

Each of the superior component top side and the inferior component bottom side is one of oblong and square. The superior component top side and the inferior component bottom side may be substantially the same shape and, more specifically, of substantially the same dimensions. Where the superior component top side and the inferior component bottom side are oblong, each of the superior component top side and the inferior component bottom side may be an oblong rectangle and more specifically a rectangle with rounded corners. Alternatively, each of the superior component top side and the inferior component bottom side may be an oblong rectangle in which each of two corners at opposite ends of a long edge of the rectangle is rounded with the other two corners not being rounded. Each of the superior component top side and the inferior component bottom side may therefore be 'D' shaped. Where the superior component top side and the inferior component bottom side are square, two corners on a same edge of the square only of the four corners of the square may be rounded or all four corners of the square may be rounded.

Each of the superior component top side and the inferior component bottom side has a major axis (i.e. a line that passes through the center of each short side of the superior component top side or the inferior component bottom side) when they are oblong whereby the superior component top side and the inferior component bottom side are wider than deep. Alternatively, the superior component top side and the inferior component bottom side are square, the square being bounded by four edges, whereby the width and depth of each of the superior component top side and the inferior component bottom side are the same.

The core component comprises a first core profile and a second core profile. The superior component bottom side comprises a superior component profile and the inferior component top side comprises an inferior component profile. The first core profile cooperates with the superior component profile and the second core profile cooperates with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device is brought into use by inserting the superior and inferior components into the intervertebral space, as described above, and without the core component. Introduction of the superior and inferior components without the core component into the intervertebral space reduces height allowing for ease of introduction and with reduced requirement for retraction of the adjacent blood vessels. Risk of damage to the adjacent blood vessels is therefore reduced. Having a superior component, an inferior component and a core component according to the invention provides improved scope for introduction of intervertebral fusion devices of larger footprint, and hence increased vertebra contact area, and also for introduction of intervertebral fusion devices which provide greater correction angles.

Having an oblong shape for the superior component top side and the inferior component bottom side means the superior component top side and the inferior component bottom side are wider than deep whereby they are more likely to conform to the shape and size of the intervertebral space than a narrow, square or circular superior component top side and inferior component bottom side. Conformance to the shape and size of the intervertebral space means the interbody fusion device is more likely to be situated over a greater extent of strong bone towards the periphery of the vertebrae defining the intervertebral space. There may therefore be reduced risk of the interbody fusion device subsiding into vertebrae after surgery. The superior and inferior components may thus confer the benefit of anteriorly inserted interbody fusion devices.

When the superior and inferior components have been positioned appropriately in the intervertebral space, the core component is inserted between the superior and inferior components. The profiles of the core component, the superior component bottom side and the inferior component top side cooperate to determine the direction of insertion such that it is oblique to the major axis of the superior component top side and the inferior component bottom side where the superior component top side and the inferior component bottom side are oblong or such that the direction of insertion is oblique to an edge of the superior component top side and the inferior component bottom side where the superior component top side and the inferior component bottom side are square. Oblique insertion of the core components, and typically with an inserter, presents a reduced risk of damage to adjacent blood vessels. Furthermore, the intervertebral fusion device is raised to a desired height by insertion of the core component in the intervertebral space thereby presenting less risk of damage than insertion of an already full height intervertebral fusion device into the intervertebral space. In addition, assembly of the intervertebral fusion device in-situ improves scope for deformity correction through selection from a range of core components providing for different extents of correction angle.

As described above, each of the superior component top side and the inferior component bottom side has a major axis whereby the superior component top side and the inferior component bottom side are wider than deep. The superior component top side and the inferior component bottom side are therefore of greater extent in the transverse direction than in the orthogonal anatomical posterior to anterior direction. Alternatively, each of the superior component top side and the inferior component bottom side is square whereby the width and depth of each of the superior component top side and the inferior component bottom side are the same.

The profiles of the core component, the superior component bottom side and the inferior component top side may cooperate to determine the direction of insertion such that it is at least 10, 20, 30, 40, 50, 60, 70 or 80 degrees to the major axis or to the edge. The direction of insertion may be 45 degrees to the major axis or edge. Where each of the superior component top side and the inferior component bottom side is an oblong rectangle, the profiles may be located on their respective components such that the core component is inserted at a corner of the oblong rectangle.

The superior component top side and the inferior component bottom side may be of substantially the same extent. The profiles may be located on their respective components such that the superior and inferior components have the same orientation and such that the superior component top side and the inferior component bottom side are in registration with each other during insertion of the core component between the superior and inferior components.

Having a core component of smaller extent than each of the superior and inferior components may provide for ease of in-situ insertion of the core component between the superior and inferior components with reduced risk of damage to adjacent blood vessels. The core component may have a core component top side and a core component bottom side, the core component top side facing the superior component bottom side and the core component bottom side facing the inferior component top side when the core component is received between the superior and inferior components. Each of the core component top side and the core component bottom side may extend over an area that is at least 5%, 10%, 15% or 20% smaller and more specifically 25% smaller than an area of each of the superior component bottom side and the inferior component top side.

Where the superior component top side and the inferior component bottom side are oblong rectangles and when the core component is received between the superior and inferior components, each of the superior component top side and the inferior component bottom side may extend beyond the core component. The core component may therefore be narrower than each of the superior and inferior components whereby the core component is more readily received in the intervertebral space with reduced likelihood of damage to adjacent blood vessels. Each of the superior component top side and the inferior component bottom side may extend beyond the core component towards each of a first pair of diagonally opposite corners of the superior component top side and the inferior component bottom side. More specifically, each of the superior component top side and the inferior component bottom side may not extend beyond or may extend to substantially a same extent as the core component at at least one of a second pair of diagonally opposite corners of the superior component top side and the inferior component bottom side. The direction of insertion of the core component as determined by the cooperating surface profiles may extend between the corners in the second pair of pair of diagonally opposite corners.

As described above, the first core profile cooperates with the superior component profile and the second core profile cooperates with the inferior component profile during insertion of the core component between the superior and inferior components whereby the core component moves in a direction oblique to the major axis or to the edge. The superior component profile may comprise a first superior component formation and a second superior component formation, the first and second superior component formations being spaced apart from each other. The core component may be received between the first and second superior component formations during insertion. The first and second superior component formations may therefore oppose each other with the first and second superior component formations defining a track along which the core component moves during insertion. The track may be linear or curvilinear.

The core component may have first and second lateral sides which face in opposite directions and which each face in a direction orthogonal to a direction of insertion of the core component and to a direction of separation of the inferior and superior components. A first superior core formation may be on the first lateral side and a second superior core formation may be on the second lateral side. The first superior component formation and the first superior core formation may cooperate and the second superior component formation and the second superior core formation may cooperate to limit movement of the core component relative to the superior component in a direction orthogonal to the direction of insertion while the core component is being inserted. More specifically, the superior component formations and the superior core formations may provide a snug fit for the core component in the orthogonal direction. The first superior component formation and the first superior core formation may therefore abut and the second superior component formation and the second superior core formation may abut whilst allowing for movement of the core component relative to the superior component. The superior component formations and the superior core formations may be of corresponding shape and more specifically one of linear and curved depending on whether the track along which the core component moves is linear or curvilinear.

The inferior component profile may comprise a first inferior component formation and a second inferior component formation, the first and second inferior component formations being spaced apart from each other. The core component may be received between the first and second inferior component formations during insertion. The first and second inferior component formations may therefore oppose each other with the first and second inferior component formations defining a track and more specifically a linear or curvilinear track along which the core component moves during insertion. A first inferior core formation may be on the first lateral side of the core component and a second inferior core formation may be on the second lateral side of the core component. The first inferior component formation and the first inferior core formation may cooperate and the second inferior component formation and the second inferior core formation may cooperate to limit movement of the core component relative to the inferior component in a direction orthogonal to the direction of insertion while the core component is being inserted. More specifically, the inferior component formations and the inferior core formations may provide a snug fit for the core component in the orthogonal direction. The first inferior component formation and the first inferior core formation may therefore abut and the second inferior component formation and the second inferior core formation may abut whilst allowing for movement of the core component relative to the inferior component. The inferior component formations and the inferior core formations may be of corresponding shape and more specifically one of linear and curved depending on whether the track along which the core component moves is linear or curvilinear.

The first superior core formation and the first inferior core formation may be spaced apart on the first lateral side of the core component in a direction of separation of the superior and inferior components. The second superior core formation and the second inferior core formation may be spaced apart on the second lateral side of the core component in a direction of separation of the superior and inferior components.

The core component top side and the core component bottom side may be inclined to each other. The core component may therefore have the form of a wedge. The core component top side and the core component bottom side may not meet at an acute angle whereby the core component has the form of a frustum of a wedge. The core component and the inferior and superior components may be configured for insertion of the core component to be led by the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having top and bottom sides of different relative inclinations. Alternatively or in addition, at least one of the inferior and superior components may be wedge shaped to provide for inclination of the core component top side and the core component bottom side in relation to each other.

A leading edge of the core component, for example the thinner edge when the core component is wedge shaped, may have at least one rounded corner. Such a radius on a corner of the leading edge may provide for ease of insertion of the core component between the inferior and superior components and also ease of separation of adjacent blood vessels with reduced risk of damage to the adjacent blood vessels.

The superior component, the inferior component and the core component may be separate components. Furthermore, the superior component and the inferior component may be disconnected from each other in the absence of the core component. Having separate inferior and superior components and core component and more specifically disconnected inferior and superior components means that the components may be introduced to the intervertebral space more gently compared with known single piece intervertebral fusion devices which often need to be hammered into place. A less gentle insertion process may damage the intervertebral fusion device, may increase time required for the intervertebral fusion device to settle in the intervertebral space, and may result in trauma to vertebral bodies or adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and differences in degree of spinal alignment and/or correction.

Each of the superior component, the inferior component and the core component may be integrally formed. The superior component and the inferior component may not be attached to each other, other than by way of the core component.

Each of the inferior and superior components may have the form of a plate, albeit a plate having structures thereon that provide for mechanical engagement with the core component, whereby it is thin relative to its width and depth. At least one of the superior component top side and the inferior component bottom side may be shaped in the coronal or sagittal planes, for example domed, to enhance fit and contact with adjacent vertebrae.

At least one of the superior component top side and the inferior component bottom side may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP).

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK or carbon reinforced PEEK. In forms of the invention, the core component may be formed by 3D printing whereby the core component has the form of a 3D lattice. The aforementioned materials may be used to form the core component by way of 3D printing.

Each of the superior component top side and the inferior component bottom side may have a width of between 24 mm and 44 mm and a depth of between 20 mm and 32 mm. Where the superior component top side and the inferior component bottom side are oblong, a ratio of width to depth may be between 1.15 to 2.

The core component may have a width of between 20 mm and 40 mm and a depth of between 10 mm and 25 mm.

When assembled, i.e. when the core component is fully received between the superior and inferior components, the intervertebral fusion device may have a height between 5 mm and 12 mm. The height may be measured at the back of the intervertebral fusion device, i.e. the part of the intervertebral fusion device first received in the intervertebral space upon insertion. The intervertebral fusion device may have a corrective angle of between 0 degrees and 30 degrees.

According to a second aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

positioning the superior component and the inferior component relative to each other in the intervertebral space such that the superior component bottom side and the inferior component top side oppose each other; and inserting the core component between the superior and inferior components whereby a separation between the superior and inferior components is determined and the superior component top side abuts against the first vertebra and the inferior component bottom side abuts against the second vertebra, wherein each of the superior component top side and the inferior component bottom side is one of: oblong having a major axis; and square, being bounded by four edges, and wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square.

The intervertebral fusion device comprises a superior component having a superior component top side and a superior component bottom side, an inferior component having an inferior component top side and an inferior component bottom side, and a core component. The method of installing the intervertebral fusion device in an intervertebral space between first and second adjacent vertebrae comprises positioning the superior component and the inferior component relative to each other in the intervertebral space such that the superior component bottom side and the inferior component top side oppose each other. The superior component and the inferior component may be moved such that they have a desired orientation in the intervertebral space whereby there is no need for a change of orientation after the core component is inserted between the superior and inferior components. The method may therefore further comprise changing an orientation of the superior component and the inferior component in the intervertebral space. The core component is inserted between the superior and inferior components to determine a separation between the superior and inferior components and such that the superior component top side abuts against the first vertebra and the inferior component bottom side abuts against the second vertebra. The method may further comprise making no change in orientation of the intervertebral fusion device during or after insertion of the core component between the superior and inferior components.

Each of the superior component top side and the inferior component bottom side has a major axis (i.e. a line that passes through the center of each short side of the superior component top side or the inferior component bottom side) when they are oblong whereby the superior component top side and the inferior component bottom side are wider than deep. Alternatively, the superior component top side and the inferior component bottom side are square, the square being bounded by four edges, whereby the width and depth of each of the superior component top side and the inferior component bottom side are the same. Alternatively, the superior component top side and the inferior component bottom side may be of different shape, for example oblongs of different shape. By way of further example, one of the superior component top side and the inferior component bottom side may be square and the other of the superior component top side and the inferior component bottom side may be oblong.

The core component comprises a first core profile and a second core profile. The superior component bottom side comprises a superior component profile and the inferior component top side comprises an inferior component profile. The first core profile cooperates with the superior component profile and the second core profile cooperates with the inferior component profile during insertion of the core component between the superior and inferior components whereby the core component moves in a direction oblique to the major axis where the superior component top side or the inferior component bottom side is oblong or to an edge of the superior component top side or the inferior component bottom side where the superior component top side or the inferior component bottom side is square. Different superior and inferior components may be selected depending on patient anatomy.

Further embodiments of the second aspect of the present invention may comprise one or more features of the first aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

Figure 1A:
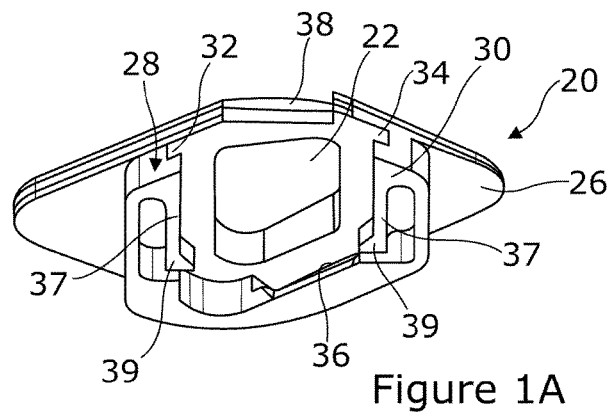
FIG. 1A is a perspective view of a superior component of an intervertebral fusion device according to a first embodiment of the present invention.

A superior component, an inferior component and a core component of a first embodiment of intervertebral fusion device 10 are shown respectively in FIGS. 1A to 1C, 2A to 2C and 3A to 3C. FIG. 4A shows the core component of FIGS. 3A to 3C before insertion between the superior and inferior components of FIGS. 1A to 2C. FIG. 4B shows the core component of FIG. 4A after insertion between the superior and inferior components of FIG. 4A.

As mentioned above, the intervertebral fusion device 10 of FIGS. 1A to 4B comprises a superior component 20, an inferior component 40 and a core component 60. Each of the superior component 20 and the inferior component 40 is generally of the form of a plate, albeit a plate having structures thereon and a large aperture 22, 42 therethrough. The superior component 20 has a superior component top side 24 and the inferior component 40 has an inferior component bottom side 44. The core component 60 has the form of a frustum of a wedge. Use of core components of different thicknesses and/or different extents of tapering wedge and with the same superior component 20 and inferior component 40 provides for different heights and angles of intervertebral fusion device 10. When the intervertebral fusion device 10 is being brought into use, the superior component and the inferior component 40 are placed in the intervertebral space and are set at a desired orientation relative to the vertebrae defining the intervertebral space. The core component 60 is maneuvered past adjacent blood vessels and positioned relative to the superior component 20 and the inferior component 40 as shown in FIG. 4A. Then the core component 60 is positioned between edges of the superior component 20 and the inferior component 40 with the thin radiused edge of the core component foremost, before the core component is progressively inserted between the superior component and the inferior component until fully received between the superior component and the inferior component. FIG. 4B shows the intervertebral fusion device 10 when the core component 60 is fully received between the superior component 20 and the inferior component 40. When the intervertebral fusion device is in the disposition shown in FIG. 4B, the superior component top side 24 abuts against a first vertebra defining the intervertebral space in part and the inferior component bottom side 44 abuts against a second vertebra defining the intervertebral space in part.

Figure 1B:
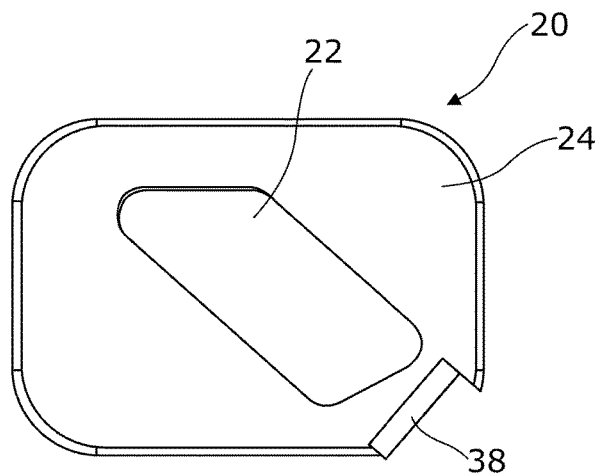
FIG. 1B is a view from above of the superior component of FIG. 1A.
Figure 1C:
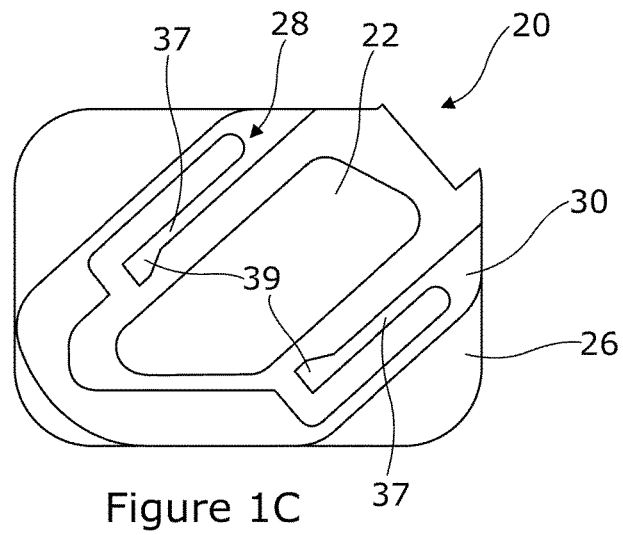
FIG. 1C is a view from below of the superior component of FIG. 1A.

The superior component 20 will now be described further with reference to FIGS. 1A to 1C. The superior component 20 has a superior component top side 24, a superior component bottom side 26, a first lateral side 28 and a second lateral side 30. The first and second lateral sides 28, 30 are spaced apart from respective corners of the superior component top side 24 whereby the superior component bottom side 26 is planar between a lateral side 28, 30 and a corner. The superior component 20 comprises a first superior component formation 32 and a second superior component formation 34. The first superior component formation 32 is on the first lateral side 28 and the second superior component formation 34 is on the second lateral side 30. The first superior component formation 32 and the first superior core formation, the latter of which is described below, abut and the second superior component formation 34 and the second superior core formation, the latter of which is described below, abut whereby there is substantially no movement of the core component 60 relative to the superior component 20 in a direction which is both orthogonal to the direction of insertion of the core component and orthogonal to the direction of separation of the superior and inferior components. Each of the first and second superior component formations 32, 34 defines a groove which extends from the edge of the superior component 20 that first receives the core component 60 when the core component is being inserted. As will become clear from the description of the core component below, the first and second superior core formations abut against their respective first and second superior component formations and such that no parts of the first and second superior core formations are received in the grooves defined by the first and second superior component formations.

Considering the first and second superior component formations 32, 34 further, each formation is constituted by a main body in the form of a finger 37 which extends from a proximal end of the finger at an anterior edge of the superior component across the superior component towards the posterior edge of the superior component. The finger 37 therefore extends in a direction of insertion of the core component. The finger 37 is unsupported and unattached along its length with the exception of its proximal end. The superior component and the finger are formed of a material of sufficient yield strength that the finger functions as a cantilever spring. Although not shown in FIG. 1A or FIG. 1C, the finger 37 is tapered in certain forms to determine stiffness and hence extent of deflection. Furthermore, a radius of the interface between the finger and the part of the superior component from which the finger extends is determined to control stiffness of the finger. The finger 37 defines a protrusion 39 at its distal end with the protrusion extending in a transverse direction of the superior component. The fingers 37 of the first and second superior component formations 32, 34 are mirror images of each other whereby their two protrusions 39 oppose each other and extend towards each other. In view of the cantilever sprung nature of each finger 37, application of a load to the protrusion 39 in a transverse direction towards a respective lateral side deflects the finger to thus store energy in the finger to provide for urging of the protrusion 39 in the opposite direction. As described below, the finger 37 is deflected by a leading edge of the core component 60 bearing against the protrusion 39.

The superior component 20 also has a superior component rear formation 36 which extends along a back edge of the superior component, the back edge being opposite the side at which the core component is first received upon insertion. The superior component rear formation 36 comprises an edge from which an inclined surface extends. The superior component 20 also has a superior component front formation 38 at the side at which the core component is first received upon insertion of the core component. The superior component front formation 38 has the form of a recess having an edge from which an inclined surface extends to the superior component top surface 24. As can be seen from FIG. 1B, the superior component top surface 24 is a rectangle with rounded corners.

Figure 2A:
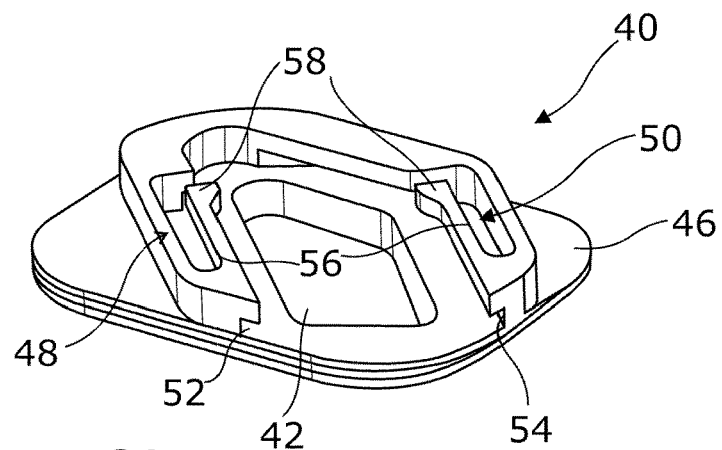
FIG. 2A is a perspective view of an inferior component of the intervertebral fusion device according to the first embodiment.
Figure 2B:
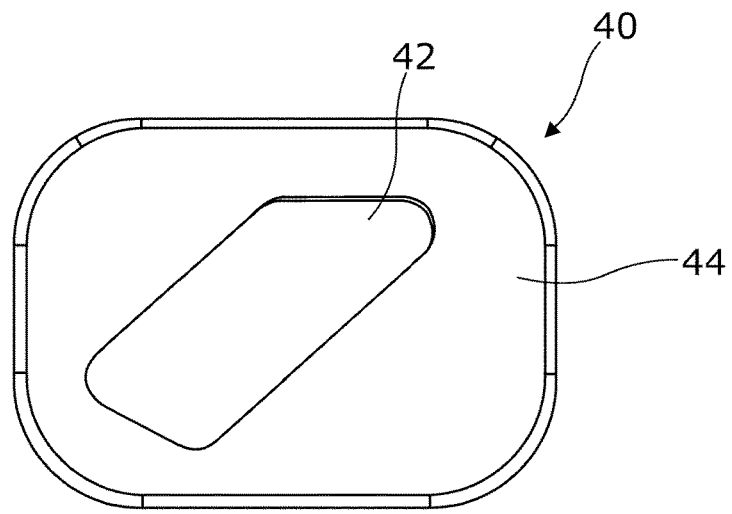
FIG. 2B is a view from above of the inferior component of FIG. 2A.
Figure 2C:
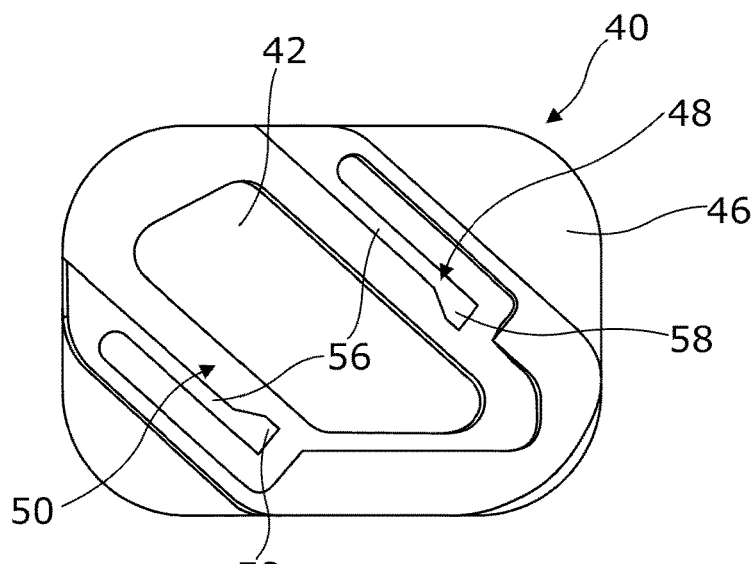
FIG. 2C is a view from below of the inferior component of FIG. 2A.

The inferior component 40 will now be described further with reference to FIGS. 2A to 2C. The inferior component 40 has an inferior component top side 46, an inferior component bottom side 44, a first lateral side 48 and a second lateral side 50. The first and second lateral sides 48, 50 are spaced apart from respective corners of the inferior component bottom side 44 whereby the inferior component top side 46 is planar between a lateral side 48, 50 and a corner. The inferior component comprises a first inferior component formation 52 and a second inferior component formation 54. The first inferior component formation 52 is towards the first lateral side 48 and the second inferior component formation 54 is towards the second lateral side 50. The first and second inferior component formations 52, 54 oppose each other and are spaced apart in a direction orthogonal to the direction of insertion of the core component between the inferior and superior components. The core component 60 is received between the first and second inferior component formations 52, 54 during insertion. Each of the first and second inferior component formations 52, 54 defines a groove which extends from the edge of the inferior component 40 that first receives the core component 60 when the core component is being inserted.

The first and second inferior component formations 52, 54 are constituted in the same fashion as the first and second superior component formations 32, 34 described above. Each of the first and second inferior component formations 52, 54 is therefore constituted by a finger 56 which extends from a proximal end of the finger at an anterior edge of the inferior component 40 across the inferior component towards the posterior edge of the inferior component. The finger 56 therefore extends in a direction of insertion of the core component. The finger 56 is unsupported and unattached along its length with the exception of its proximal end. The finger 56 defines a protrusion 58 at its distal end with the protrusion extending in a transverse direction of the superior component. The fingers 56 of the first and second inferior component formations 52, 54 are mirror images of each other whereby their two protrusions 58 oppose each other and extend towards each other. In view of the cantilever sprung nature of each finger 58, application of a load to the protrusion 58 in a transverse direction towards a respective lateral side deflects the finger to thus store energy in the finger to provide for urging of the protrusion 58 in the opposite direction. As described below, the finger 58 is deflected by a leading edge of the core component 60 bearing against the protrusion 58. As can be seen from FIG. 2B, the inferior component bottom surface 44 is a rectangle with rounded corners.

The core component 60 will now be described further with reference to FIGS. 3A to 3C. As will become apparent from the following description, the core component of FIGS. 3A to 3C differs from the core component of FIGS. 4A and 4B.

Figure 3A:
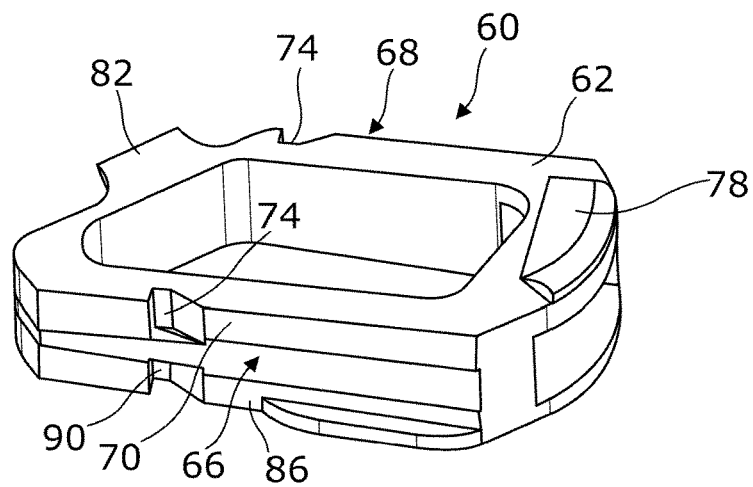
FIG. 3A is a perspective view of a core component of the intervertebral fusion device according to the first embodiment.
Figure 3B:
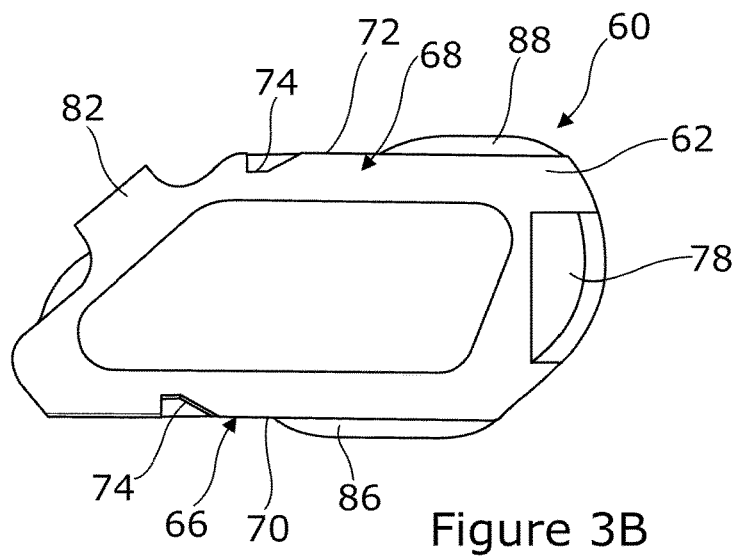
FIG. 3B is a view from above of the core component of FIG. 3A.
Figure 3C:
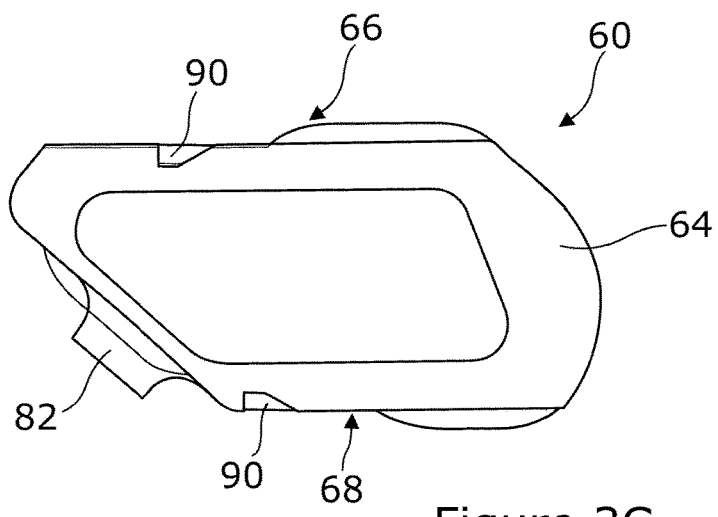
FIG. 3C is a view from below of the core component of FIG. 3A.
Figure 4A:
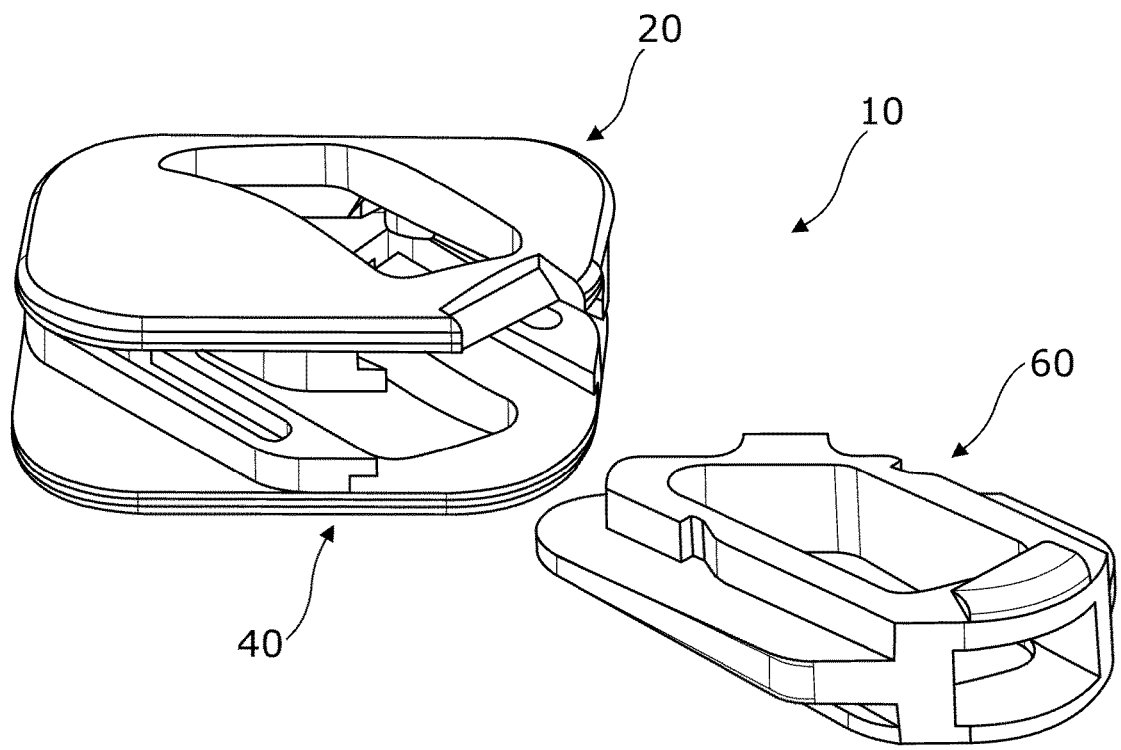
FIG. 4A shows the core component of FIGS. 3A to 3C before insertion between the superior and inferior components of FIGS. 1A to 2C.
Figure 4B:
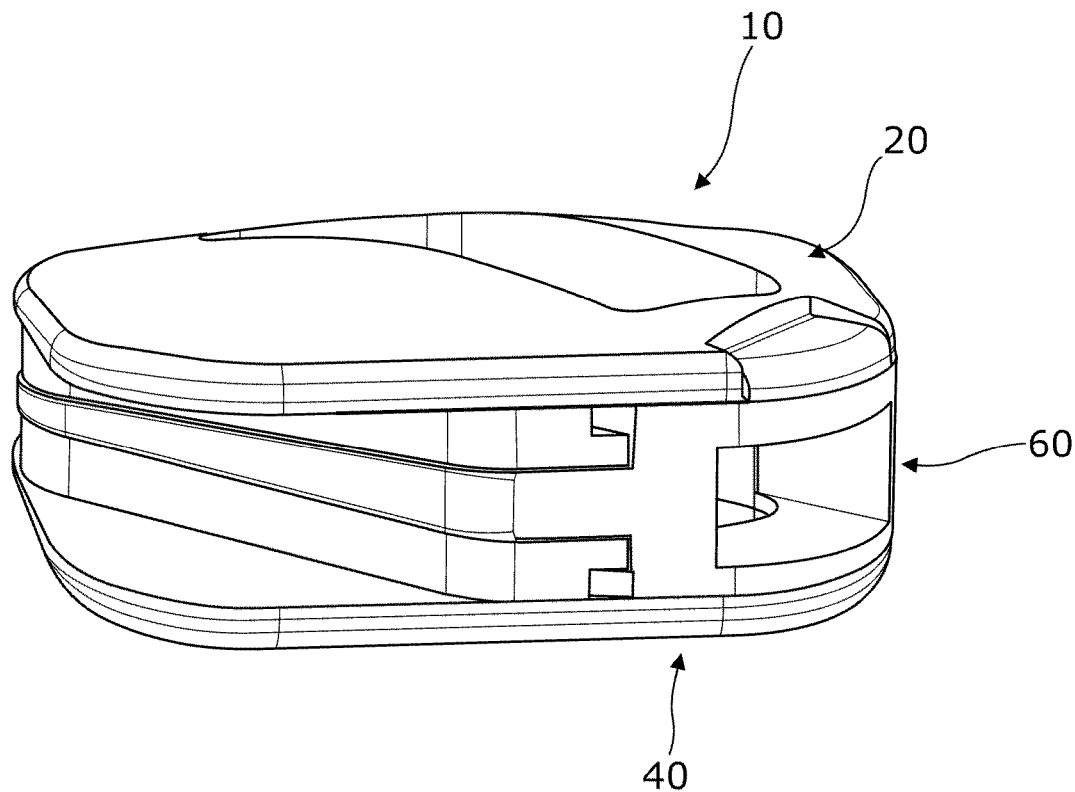
FIG. 4B shows the core component of FIG. 4A after insertion between the superior and inferior components of FIG. 4A.

Nevertheless, the core component of FIGS. 3A to 3C functions and engages with the superior and inferior components in the same way as the core component of FIGS. 4A and 4B. However, the core component of FIGS. 3A to 3C is narrower than the core component of FIGS. 4A and 4B which provides for greater ease of insertion of the core component of FIGS. 3A to 3C.

The core component 60 has a core component top side 62 and a core component bottom side 64. The core component top side 62 faces the superior component bottom side 26 and the core component bottom side 64 faces the inferior component top side 46 when the core component is received between the superior and inferior components 20, 40 as shown in FIG. 4B. As can be seen from FIGS. 3B and 3C, the depth of the core component is greater than its width. Each of the core component top side 62 and the core component bottom side 64 extends over an area that is 25% smaller than an area of each of the superior component bottom side 26 and the inferior component top side 46. Having a core component of such shape and of smaller extent than each of the superior and inferior components provides for ease of in-situ insertion of the core component between the superior and inferior components.

The core component 60 has first 66 and second 68 lateral sides which face in opposite directions and which each face in a direction orthogonal to a direction of insertion of the core component and to a direction of separation of the inferior and superior components during insertion. A first superior core formation 70 is on the first lateral side 66 and a second superior core formation 72 is on the second lateral side 68. Each of the first and second superior core formations 70, 72 comprises a planar surface that extends from near the rounded leading end of the core component to a recess 74 and a further planar surface that extends away from the recess to near a trailing end of the core component. As can be seen from FIGS. 4A and 4B, when the core component is inserted between the superior and inferior components, the first and second superior component formations 32, 34 and the first and second superior core formations 70, 72 are located on their respective superior component and core component such that the first superior component formation and the first superior core formation abut and the second superior component formation and the second superior core formation abut whilst allowing the core component to be slid progressively further between the superior and inferior components. The formations therefore cooperate to define a linear track along which the core component travels. When the core component is fully received between the superior and inferior components, each protrusion 39 on an end of a finger 37 of the superior component is received under spring bias in its respective recess 74 in the core component to thereby present resistance to expulsion of the core component from between the superior and inferior components.

The core component 60 also has an anterior formation 78 on its upper side 62 in the form of a protrusion at the anterior edge of the core component. The anterior formation 78 has a side oriented towards the posterior edge of the core component which slopes away from a distal surface of the anterior formation towards the anterior edge. As described above, the superior component 20 has a superior component front formation 38. When the core component is nearly fully inserted between the inferior and superior components, the inclined surface of the superior component front formation 38 rides over the sloping side of the anterior formation 78 to draw the superior component down onto the core component.

The core component 60 also has a posterior protrusion 82 which slopes away from a distal edge of the posterior protrusion 82 lying in the plane of the core component top side 62. As described above, the superior component 20 has a superior component rear formation 36 which extends along a back edge of the superior component. When the core component is nearly fully inserted between the inferior and superior components, the sloping surface of the posterior protrusion 82 rides over the inclined surface of the superior component rear formation 36 to draw the superior component down onto the core component.

The core component further comprises a first inferior core formation 86 on the first lateral side 66 of the core component and a second inferior core formation 88 on the second lateral side 68 of the core component. Each of the first and second inferior core formations 86, 88 comprises a planar surface that extends from near the rounded leading end of the core component to a recess 90, and a further planar surface that extends away from the recess to an elongate protrusion which extends to near a trailing end of the core component. The elongate protrusions are shaped to be received in a respective one of the grooves defined by the first and second inferior component formations 52, 54. As can be seen from FIGS. 4A and 4B, when the core component is inserted between the superior and inferior components, the first and second inferior core formations 86, 88 and the first and second inferior component formations 52, 54 are located on their respective inferior component and core component such that the first inferior component formation and the first inferior core formation abut, with elongate protrusion slidably received in recess, and the second inferior component formation and the second inferior core formation abut, with elongate protrusion slidably received in recess. The formations therefore cooperate to define a linear track along which the core component travels while resisting separation of the core component and inferior component and restraining relative movement of the core component and inferior component in the transverse direction. When the core component is fully received between the superior and inferior components, each protrusion 58 on an end of a finger 56 of the inferior component is received under spring bias in its respective recess 90 in the core component to thereby present resistance to expulsion of the core component from between the superior and inferior components.

As can be seen from a comparison of FIG. 3A with FIG. 4A, the core component of FIG. 3A lacks the elongate protrusion of the core component of FIG. 4A that extends between the leading and trailing ends of the core component and is situated between the superior and inferior core formations on each of the first and second lateral sides. The absence of these elongate protrusions from the core component of FIG. 3A provides a narrower core component which is even more readily inserted than the core component of FIG. 4A.

Figure 5:
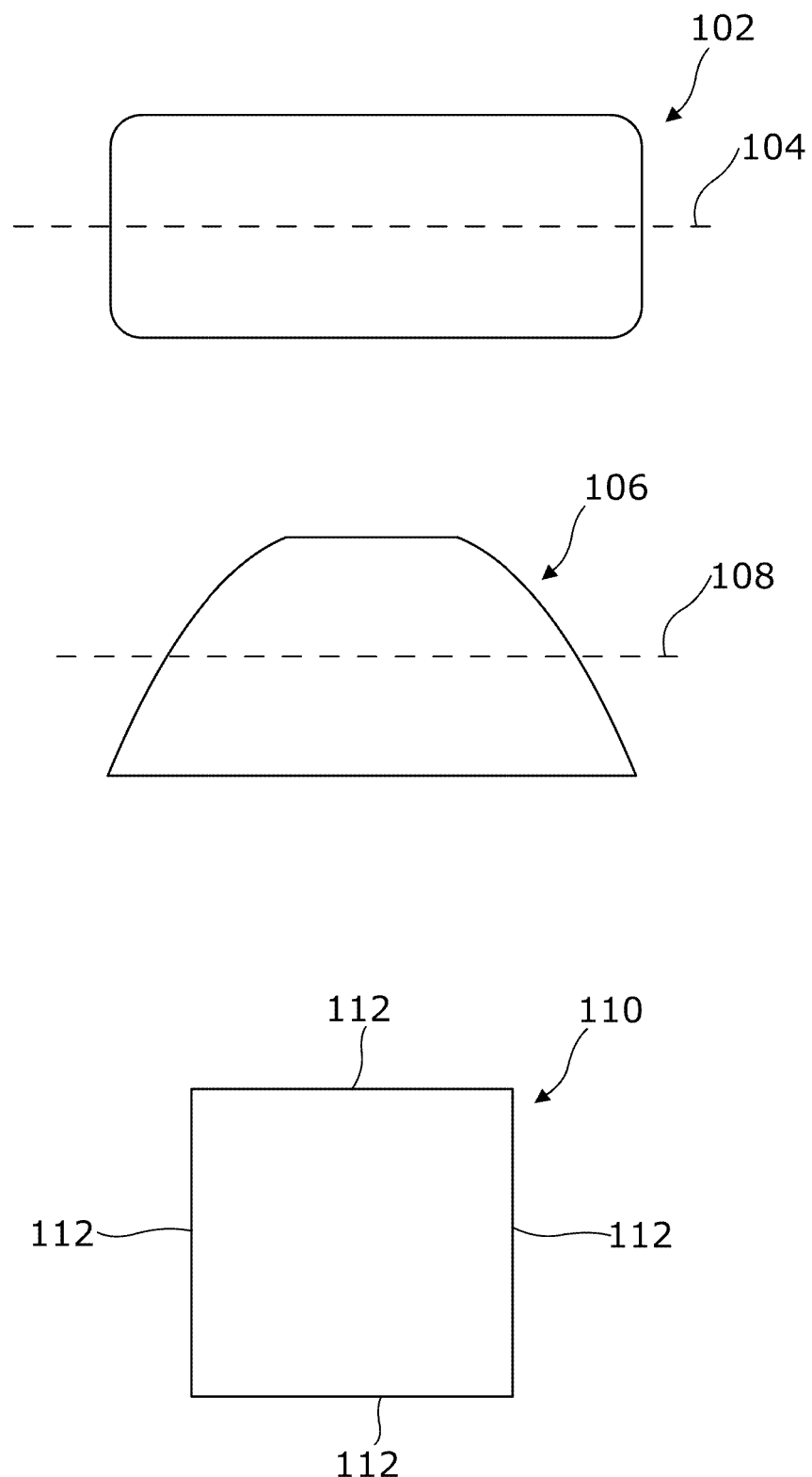
FIG. 5 shows different shapes of superior component top side and inferior component bottom side.

Different shapes of superior component top side and inferior component bottom side are shown in FIG. 5. The first shape 102 is an oblong rectangle with rounded corners. The major axis 104 (i.e. a line that passes through the center of each short side of the superior component top side/inferior component bottom side) is indicated with a dashed line. The second shape 106 is an oblong rectangle in which each of two corners at opposite ends of a long edge of the rectangle is rounded with the other two corners not being rounded. Each of the superior component top side and the inferior component bottom side may therefore have the shape shown in FIG. 5 or be more 'D' shaped. The major axis 108 is indicated with a dashed line. The direction of insertion of the core component 60 between the superior and inferior component 20, 40, as described above, is oblique to the major axis. The third shape 110 is a square in which the four edges 112 are of the same length. The direction of insertion of the core component 60 between the superior and inferior component 20, 40, as described above, is oblique to each of the four edges 112.

Figure 6A:
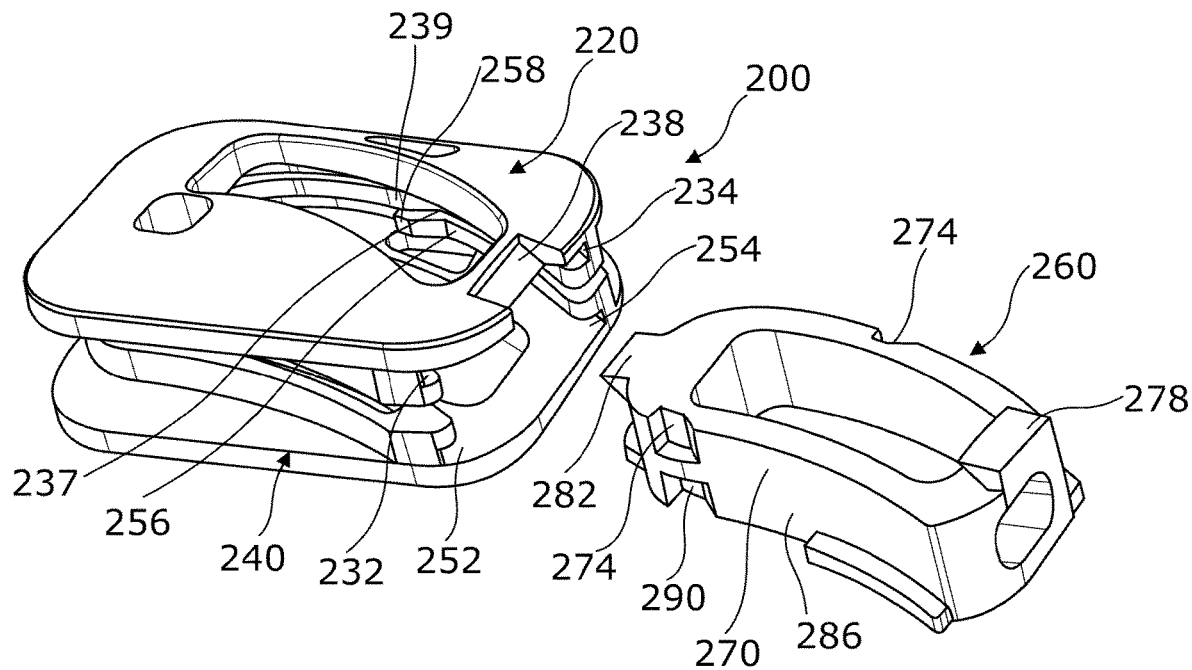
FIG. 6A shows a core component before insertion between superior and inferior components according to a second embodiment.
Figure 6B:
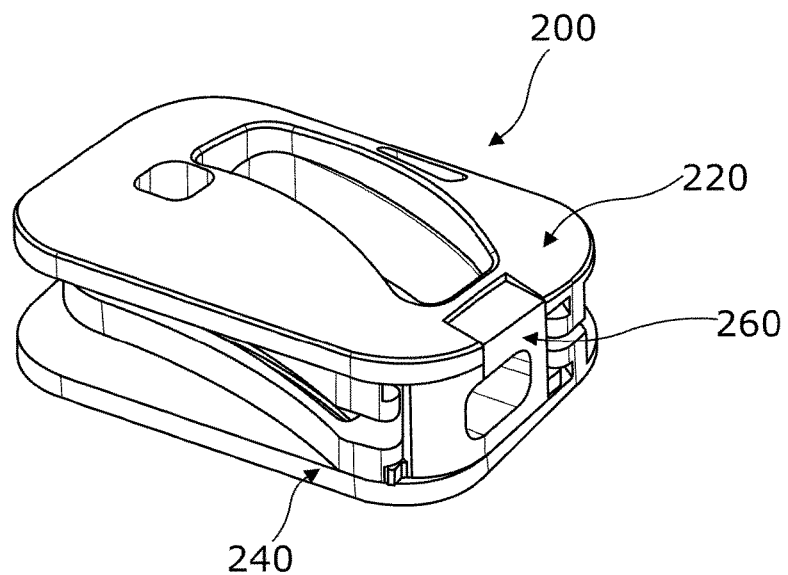
FIG. 6B shows the core component of FIG. 6A after insertion between the superior and inferior components of FIG. 6A.

A superior component, an inferior component and a core component of a second embodiment of intervertebral fusion device 200 are shown in FIG. 6A before insertion of the core component between the superior and inferior components. FIG. 6B shows the core component of FIG. 6A after insertion between the superior and inferior components of FIG. 6A.

As can be seen from FIG. 6A, the superior component top side and inferior component bottom side are of the same shape as the first embodiment.

Furthermore, the superior component 220, the inferior component 240 and the core component 260 comprise the same features as the first embodiment. For example, the first and second superior component formations 232, 234 in the second embodiment are each constituted by a main body in the form of a sprung finger 237 with the finger having a protrusion 239 at its end. The first and second inferior component formations 252, 254 in the second embodiment are each constituted by a finger 256 with the finger having a protrusion 258 at its end. By way of further example, the superior component of the second embodiment has a superior component front formation 238 in the form of a recess which cooperates with an anterior formation 278 on the core component to draw the superior component and core component together. The core component of the second embodiment also has a posterior protrusion 282 which cooperates with a superior component rear formation to draw the superior component and core component together.

By way of yet further example, each of the first 270 and second superior core formations of the second embodiment comprises a planar surface that extends from near the leading end of the core component to a recess 274 and a further planar surface that extends away from the recess to near a trailing end of the core component. Each of the first 286 and second inferior core formations of the second embodiment comprises a planar surface that extends from near the leading end of the core component to a recess 290, and a further planar surface that extends away from the recess to an elongate protrusion which extends to near a trailing end of the core component. The form of the second embodiment is such that the core component engages with the superior and inferior components as described above with reference to the first embodiment.

The key difference between the first and second embodiments is the core component following a curved path during insertion of the core component between the superior and inferior components in the second embodiment. The curved path is provided by the first and second superior and inferior component formations 232, 234, 252, 254 being curved with the first and second superior and inferior core formations having corresponding curvatures. The first and second superior and inferior component formations 232, 234, 252, 254 therefore cooperate with their respective first and second superior and inferior core formations by abutting as described with reference to the first embodiment to constrain the core component to follow a curvilinear path during insertion of the core component between the superior and inferior components.

The invention claimed is:

1. An intervertebral fusion device comprising:
   a superior component having a superior component top side and a superior component bottom side, the superior component configured to be received in an intervertebral space between first and second vertebrae whereby the superior component top side abuts against the first vertebra;
   an inferior component having an inferior component top side and an inferior component bottom side, the inferior component configured to be received in the intervertebral space between the first and second vertebrae whereby the inferior component bottom side abuts against the second vertebra, the superior component bottom side and the inferior component top side opposing each other when the superior and inferior components are received in the intervertebral space;
   a core component configured for insertion between the superior and inferior components whereby a separation between the superior and inferior components and hence height of the intervertebral fusion device are determined when the intervertebral fusion device is in the intervertebral space,
   wherein each of the superior component top side and the inferior component bottom side is oblong having a major axis, and
   wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis, wherein when the core component is received between the superior and inferior components, each of the superior component top side and the inferior component bottom side extends beyond the core component towards each corner of a first pair of diagonally opposite corners of each of the superior component top side and the inferior component bottom side, each of the superior component top side and the inferior component bottom side extends to substantially a same extent as the core component at at least one corner of a second pair of diagonally opposite corners of each of the superior component top side and the inferior component bottom side, and a direction of insertion of the core component as determined by the cooperating profiles extends between the corners in each pair of the second pairs of diagonally opposite corners.

2. The intervertebral fusion device according to claim 1, wherein each of the superior component top side and the inferior component bottom side is an oblong rectangle with at least three rounded corners.

3. The intervertebral fusion device according to claim 2, wherein the first and second core profiles, the superior component profile and the inferior component profile are located on their respective components such that the core component is inserted at a corner of the oblong rectangle.

4. The intervertebral fusion device according to claim 1, wherein each of the superior component top side and the inferior component bottom side is an oblong rectangle in which each of two corners at opposite ends of a long edge of the rectangle is not rounded with the other two corners being rounded.

5. The intervertebral fusion device according to claim 1, wherein the superior component top side and the inferior component bottom side are of substantially the same extent, the first and second core profiles, the superior component profile and the inferior component profile are located on their respective components such that the superior and inferior components have the same orientation and such that the superior component top side and the inferior component bottom side are in registration with each other during insertion of the core component between the superior and inferior components.

6. The intervertebral fusion device according to claim 1, wherein the superior component profile comprises a first superior component formation and a second superior component formation, the first and second superior component formations spaced apart from and opposing each other to define a track along which the core component moves during insertion between the superior and inferior components.

7. The intervertebral fusion device according to claim 6, wherein the track defined by the first and second superior component formations is curvilinear.

8. The intervertebral fusion device according to claim 6, wherein the core component has first and second lateral sides which face in opposite directions and which each face in a direction orthogonal to a direction of insertion of the core component and to a direction of separation of the inferior and superior components, wherein the core component has a first superior core formation on the first lateral side and a second superior core formation on the second lateral side, and wherein the first superior component formation and the first superior core formation cooperate and the second superior component formation and the second superior core formation cooperate to limit movement of the core component relative to the superior component in a direction orthogonal to the direction of insertion while the core component is being inserted.

9. The intervertebral fusion device according to claim 8, wherein the inferior component profile comprises a first inferior component formation and a second inferior component formation, the first and second inferior component formations spaced apart from and opposing each other to define a track along which the core component moves during insertion between the superior and inferior components, wherein the core component has a first inferior core formation on the first lateral side and a second inferior core formation on the second lateral side of the core component, and wherein the first inferior component formation and the first inferior core formation cooperate and the second inferior component formation and the second inferior core formation cooperate to limit movement of the core component relative to the inferior component in a direction orthogonal to the direction of insertion while the core component is being inserted, wherein the first superior core formation and the first inferior core formation are spaced apart on the first lateral side of the core component in a direction of separation of the superior and inferior components, and wherein the second superior core formation and the second inferior core formation are spaced apart on the second lateral side of the core component in a direction of separation of the superior and inferior components.

10. The intervertebral fusion device according to claim 1, wherein the inferior component profile comprises a first inferior component formation and a second inferior component formation, the first and second inferior component formations spaced apart from and opposing each other to define a track along which the core component moves during insertion between the superior and inferior components.

11. The intervertebral fusion device according to claim 10, wherein the core component has first and second lateral sides which face in opposite directions and which each face in a direction orthogonal to a direction of insertion of the core component and to a direction of separation of the inferior and superior components, wherein the core component has a first inferior core formation on the first lateral side and a second inferior core formation on the second lateral side of the core component, and wherein the first inferior component formation and the first inferior core formation cooperate and the second inferior component formation and the second inferior core formation cooperate while the core component is being inserted to limit movement of the core component relative to the inferior component in a direction of separation of the superior and inferior components and in a direction orthogonal to the direction of insertion and to the direction of separation of the superior and inferior components.

12. The intervertebral fusion device according to claim 1, wherein the core component has a core component top side and a core component bottom side, the core component top side facing the superior component bottom side and the core component bottom side facing the inferior component top side when the core component is received between the superior and inferior components, and wherein the core component top side and the core component bottom side are inclined to each other whereby the core component is of wedge form.

13. The intervertebral fusion device according to claim 1, wherein a leading edge of the core component first received between the superior and inferior components has at least one rounded corner.

14. The intervertebral fusion device according to claim 1, wherein the superior component, the inferior component and the core component are separate components, and wherein the superior component and the inferior component are disconnected from each other in the absence of the core component.

15. The intervertebral fusion device according to claim 1, wherein each of the superior component, the inferior component and the core component is integrally formed.

16. The intervertebral fusion device according to claim 1, wherein the core component has a core component top side and a core component bottom side, the core component top side facing the superior component bottom side and the core component bottom side facing the inferior component top side when the core component is received between the superior and inferior components, and each of the core component top side and the core component bottom side extends over an area that is at least 25% smaller than an area of each of the superior component bottom side and the inferior component top side.

17. The intervertebral fusion device according to claim 1, wherein each of the inferior and superior components has the form of a plate, albeit a plate having structures thereon that provide for mechanical engagement with the core component, whereby it is thin relative to its width and depth.

18. The intervertebral fusion device according to claim 1, wherein at least one of the superior component top side and the inferior component bottom side comprises at least one of: formations which, in use, engage with the bone of the vertebra; an aperture for passage of bone graft material therethrough from an interior of the intervertebral fusion device; and a coating thereon or an impregnation therein which provides for bone adhesion and/or bone formation, to thereby provide for fusion.

19. A method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:
positioning the superior component and the inferior component relative to each other in the intervertebral space such that the superior component bottom side and the inferior component top side oppose each other; and
inserting the core component between the superior and inferior components whereby a separation between the superior and inferior components is determined and the superior component top side abuts against the first vertebra and the inferior component bottom side abuts against the second vertebra,
wherein each of the superior component top side and the inferior component bottom side is oblong having a major axis, and
wherein the core component comprises a first core profile and a second core profile, the superior component bottom side comprises a superior component profile, the inferior component top side comprises an inferior component profile, the first core profile cooperating with the superior component profile and the second core profile cooperating with the inferior component profile during insertion of the core component between the superior and inferior components whereby the core component moves in a direction oblique to the major axis,
wherein when the core component is received between the superior and inferior components, each of the superior component top side and the inferior component bottom side extends beyond the core component towards each corner of a first pair of diagonally opposite corners of each of the superior component top side and the inferior component bottom side, each of the superior component top side and the inferior component bottom side extends to substantially a same extent as the core component at at least one corner of a second pair of diagonally opposite corners of each of the superior component top side and the inferior component bottom side, and a direction of insertion of the core component as determined by the cooperating profiles extends between the corners in each pair of the second pairs of diagonally opposite corners.

20. The method according to claim 19 further comprising moving the superior component and the inferior component in the intervertebral space such that they have a desired orientation in the intervertebral space, the desired orientation in the intervertebral space being achieved before the step of inserting the core component between the superior and inferior components.

\* \* \* \* \*